US00PP09650P

United States Patent [19]

Olesen et al.

[11] Patent Number: Plant 9,650

[45] Date of Patent: Oct. 1, 1996

[54] SHRUB ROSE PLANT NAMED 'POULEMB'

[75] Inventors: Pernille Olesen; Mogens Olesen, both of Fredensborg, Denmark

[73] Assignee: DeVor Nurseries, Inc., Watsonville, Calif.

[21] Appl. No.: 414,537

[22] Filed: Mar. 31, 1995

[51] Int. Cl.[6] ..... A01H 5/00

[52] U.S. Cl. ..... Plt./1

[58] Field of Search ..... Plt./1, 23

[56] References Cited

U.S. PATENT DOCUMENTS

| | | | |
|---|---|---|---|
| P.P. 122 | 2/1935 | Thomas, Jr. | Plt./23 |
| P.P. 4,463 | 10/1979 | Goujon | Plt./1 |
| P.P. 8,871 | 8/1994 | Kordes | Plt./1 |

*Primary Examiner*—Howard J. Locker
*Attorney, Agent, or Firm*—Christie, Parker & Hale, LLP

[57] ABSTRACT

A shrub rose variety producing white flowers.

1 Drawing Sheet

SUMMARY OF THE INVENTION

The present invention relates to a new and distinct shrub rose variety which was originated by crossing as seed and pollen parents two unnamed and undistributed seedlings of our creation. The varietal denomination of this new rose is 'Poulemb'.

Among the novel characteristics possessed by this new variety which distinguish it from its parents and all other varieties of which we are aware are its attractive white flowers borne on a bushy, vigorous plant.

Asexual reproduction by budding of the new variety as performed in Watsonville, Calif., shows that the foregoing and other distinguishing characteristics come true to form and are established and transmitted through succeeding propagations. Other known forms of asexual reproduction may be also employed.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—Unnamed, unpatented seedling.

Class: Shrub.

The following is a detailed description of the new variety, from specimens grown outdoors in Watsonville, Calif., in the month of September. The color terminology used is in accordance with the Royal Horticultural Society Colour Chart (RHSCC), and refers to plate numbers in the aforementioned color chart. Phenotypic expression may vary depending on light, environmental and cultural conditions.

FLOWER

Blooming habit: Recurrent.

A. Bud:

(1) *Size.*—Small.

(2) *Form.*—Ovoid.

(3) *Color.*—When sepals first divide, bud color is near 155C.

(4) *Sepals.*—Sepals open outward, asymmetric with shaped tip; about 0.5 cm. Color: Near 139C.

(5) *Peduncle.*—Length: About 2.5 cm to about 3.5 cm. Aspect: Smooth. Strength: Erect, sturdy. Color: Near 136B.

(6) *Bracts.*—About 10 to 15; near 137A, elliptical with leaf pointed ends; about 2.5 cm to 3.5 cm below calyx.

B. Bloom:

(1) *Size.*—Average size when fully expanded — about 2.5 cm.

(2) *Borne.*—Clusters of about 3 to 7 blooms per cluster.

(3 *Form.*—Imbricated, petals ruffled at maturity, rounded to ovoid becoming cupped at maturity unfurling to reveal the center.

(4) *Petalage.13* Number of petals under normal condition — about 5 to 6.

(5) *color* (⅓–½ *open*).—Outer petals—Top surface: near 155B; Undersurface: near 155B. Inner petals—Top surface: near 155B; Undersurface: near 155B. Base of petals: Near 157D. General tonality from a distance: White.

(6) *Color* (*fully open*).—Outer petals—Top surface: near 155B; Undersurface: near 155B. Base of petals Near 157D. General tonality from a distance: White.

i Color change.—Color remains constant. Petal top surface: Constant. Petal undersurface: Constant. General tonality at a distance: White.

C. Petals:

(1) *Texture.*—Medium smooth petals.

(2) *Appearance.*—Matte.

(3) *Form.*—Broad with emarginate apex.

(4) *Arrangement.*—Irregular, loose.

(5) *Petaloids.*—None.

(6) *Fragrance.*—None.

(7) *Lasting quality.*—Long lasting on plant.

(8) *Persistence.*—Petals drop off cleanly.

REPRODUCTIVE ORGANS

A. Stamens:

(1) *Arrangement.*—Irregularly arranged around styles.

(2) *Stamens.*—Near 17B.

(3) *Anthers.*—Near 17B (4) *Filaments.*—Near 5C.

(5) *Pollen.*—Near 17B.

B. Pistils: (1) *Styles.*—United into a column which extends above the mouth of the receptacle.

(2) *Stigmas.*—near 145B.

C. Characteristics of hips: Not observed.

PLANT

A Form: Compact.

B. Growth: Very vigorous; about 61 cm to about 76 cm in height at first season.

C. Foliage: Compound 3 to 9 l leaflets.

(1) *Size.*—Small.

(2) *Quantity.*—Abundant.

(3) *Color.*—New foliage — upper side near 135A underside near 136B; old foliage — upper side near 136A, underside near 137A.

(4) *Shape.*—Oval.

(5) *Texture.*—Upper side glossy, smooth; under side matte.

(6) *Edge.*—Serrate.

(7) *Serration.*—Dentate.

(8) *Leaf stem.*—Color — medium green.

(9) *Stipules.*—Adnate and smooth.

(10) *Rachis.*—Smooth.

(11) *Petioles.*—Top near 137A, underside near 146B.

(12) *Auricle.*—Narrow, triangular, facing forward and bearded with glandular bristles.

(13) *Resistance to disease.*—Very resistant to black-spot, mildew and rust.

D. Wood:

(1) *New wood.*—Color near 137D, bark smooth.

(2) *Old wood.*—Color near 147A to 147B, bark smooth.

E. Thorns:

(1) *Thorns.*—Quantity: On main stalk, few; laterals from stalk, none. Form: Slightly curved downward. Length: Medium. Color: near 152D. Position: Irregular.

(2) *Prickles.—None.*

G. Winter hardiness: Winter hardy in denmark and in Watsonville, Calif.

I claim:

1. A new and distinct shrub rose variety, substantially as shown and described.

* * * * *

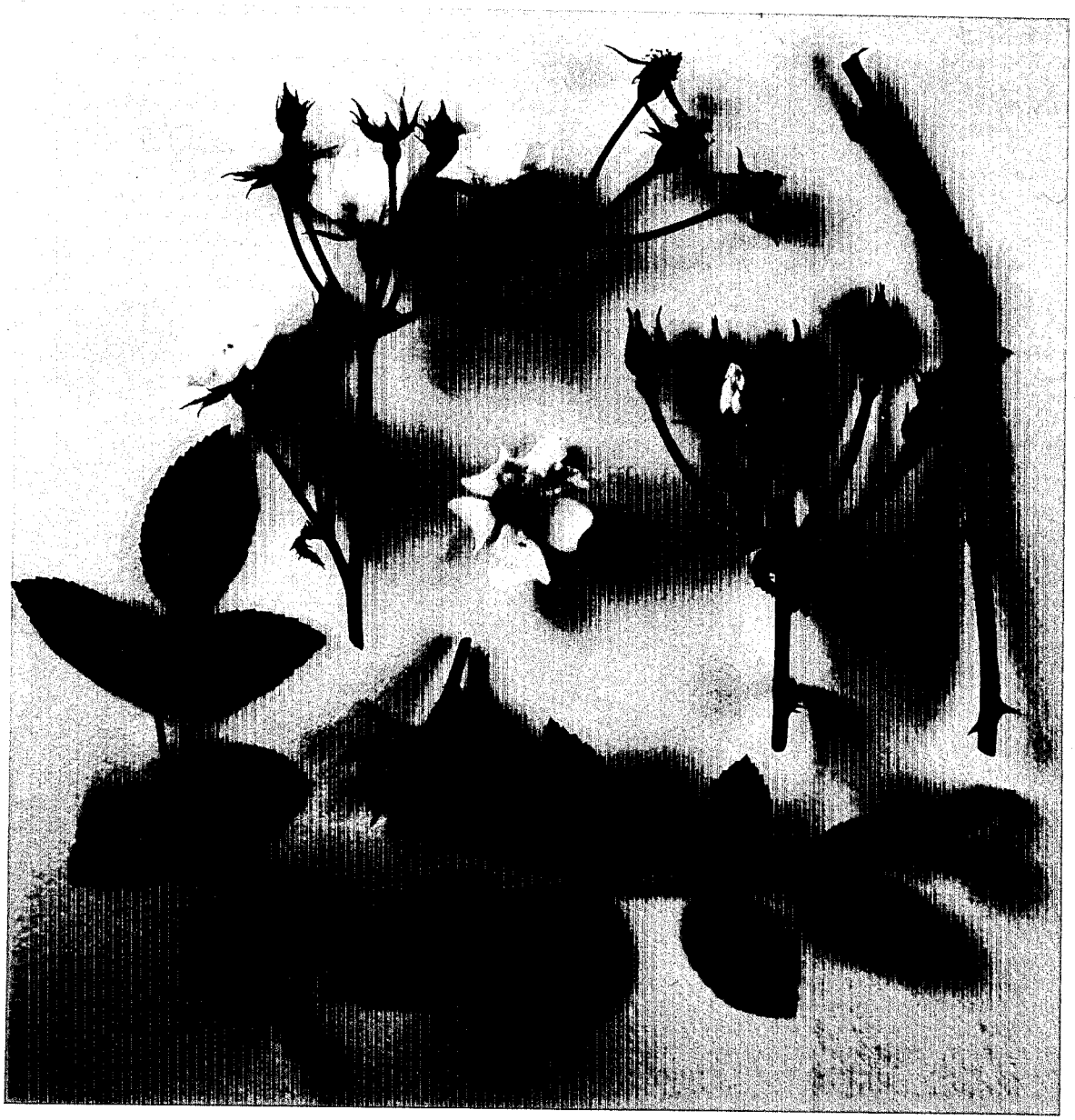

UNITED STATES PATENT AND TRADEMARK OFFICE

CERTIFICATE OF CORRECTION

PATENT NO. : Plant 9,650

DATED : October 1, 1996

INVENTOR(S) : Pernille Olesen; Mogens Olesen

It is certified that error appears in the above-indentified patent and that said Letters Patent is hereby corrected as shown below:

Column 2, line 26, before "Color" delete "i" and insert therefor -- (7) --.
Column 3, line 9, before "leaflets" delete "l".
Column 3, line 15, change "under side" to -- underside --.
Column 4, line 15, change "denmark" to -- Denmark --.

Signed and Sealed this

Eleventh Day of March, 1997

*Attest:*

Bruce Lehman

BRUCE LEHMAN

*Attesting Officer*

*Commissioner of Patents and Trademarks*